United States Patent [19]

Brite

[11] 4,438,090

[45] Mar. 20, 1984

[54] METHOD OF PREPARING AN INSECTICIDE CONTAINING BORIC ACID

[76] Inventor: Alan D. Brite, 5147 W. Jefferson Blvd., Los Angeles, Calif. 90016

[21] Appl. No.: 372,948

[22] Filed: Apr. 29, 1982

Related U.S. Application Data

[63] Continuation-in-part of Ser. No. 24,962, Mar. 29, 1979, abandoned, which is a continuation-in-part of Ser. No. 870,740, Jan. 19, 1978, abandoned.

[51] Int. Cl.³ .................. G01N 31/00; G01N 31/22; G01N 33/48; A01N 59/14
[52] U.S. Cl. ............................ 424/7.1; 424/10; 424/148
[58] Field of Search ................... 424/7, 10, 148

[56] References Cited

U.S. PATENT DOCUMENTS

| | | | |
|---|---|---|---|
| 490,688 | 1/1893 | Smith | 424/148 |
| 1,029,203 | 6/1912 | Loewenthal | 424/148 |
| 1,204,794 | 11/1916 | Levy | 424/10 |
| 1,893,008 | 1/1933 | Wamoscher | 424/10 |
| 2,015,062 | 9/1935 | Benjamin | 424/7 |
| 2,088,651 | 8/1937 | Henninger | 424/7 |
| 3,090,722 | 5/1963 | Baker | 424/7 |

FOREIGN PATENT DOCUMENTS 2021   4/1900   Fed. Rep. of Germany ........ 424/10

OTHER PUBLICATIONS

Chem. Abst. 63, 6 265 (g) (1965)–CIBA Ltd.
Chem. Abst. 83, 2 367 (n) (1975)–Hazebuchi.

*Primary Examiner*—Douglas W. Robinson
*Attorney, Agent, or Firm*—Lyon & Lyon

[57] ABSTRACT

A method of preparing an insecticide containing boric acid which comprises milling boric acid to a particle size between about 100 to about 400 mesh; blending said boric acid particles with a member selected from the group consisting of magnesium stearate, silica gel, and tricalcium phosphate, with sucrose octa-acetate or denatonium benzoate, and with a non-white powdered pigment sufficiently soon after said boric acid is milled so that said boric acid particles remain smaller than about 100 mesh; and electrically charging said blend to induce an electrostatic charge on the discrete particles of the insecticide.

7 Claims, No Drawings

METHOD OF PREPARING AN INSECTICIDE CONTAINING BORIC ACID

CROSS-REFERENCE TO RELATED APPLICATIONS

This application is a continuation-in-part of U.S. patent application, Ser. No. 24,962, filed Mar. 29, 1979, which application is a continuation-in-part of my earlier filed U.S. patent application, Ser. No. 870,740, filed Jan. 19, 1978, now both abandoned.

DETAILED DESCRIPTION OF THE INVENTION

The present invention is directed to a method of preparing an insecticide containing boric acid which is particularly effective in controlling cockroaches. In general, the steps of the method are as follows. Boric acid is milled or ground to a particle size between about 100 to about 400 mesh. The ground boric acid particles are then blended with a member selected from the group consisting of magnesium stearate, silica gel, and tricalcium phosphate; sucrose octa-acetate or denatonium benzoate; and a non-white powdered pigment sufficiently soon after the boric acid is milled so that the boric acid particles remain smaller than about 100 mesh. If the ground boric acid particles are not blended with the remaining components of the insecticide soon enough, the boric acid particles tend to cake and form lumps greater in size than about 100 mesh. In particular, it has been found that if the ground boric acid particles are permitted to sit overnight before being blended with the other components of the insecticide, lumps greater in size than about 100 mesh will have formed in the boric acid particles. Preferably, the milled boric acid is blended with the remaining components of the insecticide within about two hours after milling. After the components of the insecticide have been blended together, an electrostatic charge is induced on the particles thereof by passing an electric current through the blend. Preferably, the blend is electrically charged before it is put into an individual container as well as being further charged after it has been placed in the container.

It has been found that the insecticide prepared by the method of the present invention is particularly effective against cockroaches. Although boric acid powder alone does not repel cockroaches, as the percentage of boric acid in the insecticide decreases, the probability that the additional component(s) will cause the insecticide to become repellent increases. The addition of a component which tends to cause the insecticide to repel cockroaches, instead of killing them, is undesirable and would diminish the effectiveness of the insecticide. While known insecticides containing boric acid and magnesium stearate are effective and do not repel cockroaches, they are particularly hazardous for household use because of their toxicity. However, it has been found that sucrose octa-acetate and denatonium benzoate are compatible with boric acid powder in that insecticides containing boric acid and one of these components do not appear to repel cockroaches. While sucrose octa-acetate and denatonium benzoate (also known as Bitrex) do not diminish the effectiveness of the insecticide, they exhibit a taste which is repulsive to humans or domestic animals thereby preventing inadvertent consumption of a quantity of insecticide which could render harm. Sucrose octa-acetate is particularly effective in not repelling cockroaches although the reason for this is not understood. It has also been found that sucrose octa-acetate, although a hygroscopic compound, does not render the blended insecticide hydrophilic when combined with the boric acid and either magnesium stearate, silica gel or tricalcium phosphate. It is imperative that the blended insecticide not have an affinity for water as, for example, where the humidity may reach high levels, because the addition of water to the blended insecticide causes the mixture to cake with the result that lumps larger in size than about 100 mesh are left after the mixture has dried out. Since the particles of the insecticide must be small enough to become attached to the bodies of the cockroaches, lumps larger in size than 100 mesh substantially diminish the effectiveness of the insecticide. Preferably, all of the particles of the blended insecticide are smaller in size than 100 mesh.

The non-white powdered pigment helps to prevent inadvertent consumption of the insecticide as it distinguishes the insecticide from common household food items such as flour, sugar, salt, and the like. It is particularly preferred that the powdered pigment be of a blue color. A suitable blue powdered pigment which does not appear to cause the insecticide to become repellent can be purchased from BASF Wyandotte Corp., Pigments Division, Holland, Mich., under the name "Phthalo Blue."

Preferably, the blended insecticide comprises from about 95% to about 99% by weight of the ground boric acid, from about 0.6% to about 4% by weight of a member selected from the group of magnesium stearate, silica gel or tricalcium phosphate, and less than about 0.5% by weight each of sucrose octa-acetate or denatonium benzoate and the non-white powdered pigment. A particularly preferred insecticide comprises about 99% by weight boric acid, about 0.69% by weight magnesium stearate, about 0.30% by weight sucrose octa-acetate, and about 0.01% by weight of phthalo blue pigment.

Any suitable grinding means known to those skilled in the art may be used to mill the boric acid to a particle size from about 100 to about 400 mesh. Many such pulverizers are well known. In particular, micropulverizers manufactured by the Pulverizer Machinery Corp., Summit, N.J., models 2 or 20H, may be used.

A charging system suitable for electrostatically charging the insecticide can be obtained from The Simco Company, Inc., 4085 East La Palma Ave., Anaheim, Calif. 92807, under the trademark CHARGEMASTER ®. Those charging systems having a negative polarity with a maximum output voltage of about 25,000 volts are particularly preferred. A copper probe may be placed in the receptacle holding the insecticide after it has been blended so that an electrostatic charge can be induced on the particles of the blended insecticide before it is placed in individual containers. A further electrostatic charge may be attained after the blended insecticide has been placed in the individual containers by passing a "Chargemaster" wand, also obtainable from The Simco Company, Inc., or a similar device over the filled container. An electrical charge of about 25,000 volts is preferably used each time and has been found to induce a sufficient electrostatic charge on the particles of the insecticide which is retained, at least in part, over time. Passing the "Chargemaster" wand over the filled containers also appears to induce an electrostatic charge in the container itself which aids in retaining the electrostatic charge on the particles of the insecticide. It has been found that electrically charging the blended insecticide increases its effectiveness. It is believed that this increased effectiveness results from the electrostatically charged particles of the insecticide sticking to the bodies of the cockroaches who then carry the insecticide with them and spread it among the other cockroaches, as well as sticking to the vertical surfaces on which the cockroaches crawl.

While the preferred application of this invention has been shown and described, it would be apparent to those skilled in the art that many more modifications are possible without departing from the inventive concept herein described. The invention, therefore, is to be limited only by the lawful scope of the claims which follow.

What is claimed is:

1. A method of preparing an insecticide containing an insecticidally effective amount of boric acid which comprises:
    milling boric acid to a particle size between about 100 to about 400 mesh;
    blending said boric acid particles with effective amounts of a member selected from the group consisting of magnesium stearate, silica gel, and tricalcium phosphate, and with a taste deterent effective amount of sucrose octa-acetate or denatonium benzoate, and with a non-white powdered pigment of sufficient quantity to color the insecticide sufficiently soon after said boric acid is milled so that said boric acid particles remain smaller than about 100 mesh; and
    electrically charging said blend to induce an electrostatic charge on the discrete particles of the insecticide.

2. A method of preparing an insecticide containing boric acid as in claim 1 wherein said boric acid particles are blended with the member selected from the group consisting of magnesium stearate, silica gel, and tricalcium phosphate, and with the sucrose octa-acetate or denatonium benzoate, and with the non-white powdered pigment within two hours after said boric acid is milled.

3. A method of preparing an insecticide containing boric acid as in claim 1 wherein said blend is electrostatically charged before being put in an individual container.

4. A method of preparing an insecticide containing boric acid as in claim 3 wherein said blend is additionally electrically charged after being placed in said container.

5. A method of preparing an insecticide containing an insecticidally effective amount of boric acid which comprises:
    milling said boric acid to a particle size from about 100 to about 400 mesh;
    blending said boric acid particles with effective amounts of magnesium stearate, and with a taste deterent effective amount of sucrose octa-acetate, and with a non-white powdered pigment of sufficient quantity to color the insecticide within two hours after said boric acid is milled;
    electrically charging said blend to impart an electrostatic charge thereto before said blend is put in an individual container; and
    further electrically charging said blend after said blend is placed in said container.

6. A method of preparing an insecticide containing boric acid as in claim 5 wherein said blended insecticide comprises about 95% by weight to about 99% by weight boric acid; about 0.6% to about 4% by weight magnesium stearate, less than about 0.5% by weight sucrose octa-acetate, and less than 0.5% of the non-white powdered pigment.

7. A method of preparing an insecticide containing boric acid as in claim 5 wherein said non-white powdered pigment is blue.

* * * * *